United States Patent [19]

Kosuge et al.

[11] Patent Number: 5,451,575
[45] Date of Patent: Sep. 19, 1995

[54] METHOD OF TREATING LIVER DYSFUNCTION WITH 24-R SCYMNOL

[75] Inventors: Yoshiki Kosuge; Takuo Kosuge; Kuniro Tsuji; Hitoshi Ishida, all of Shizuoka, Japan

[73] Assignee: J. W. Broadbent Nominees Pty., Ltd., Melbourne, Australia

[21] Appl. No.: 176,576

[22] Filed: Dec. 30, 1993

Related U.S. Application Data

[63] Continuation-in-part of Ser. No. 863,318, Apr. 1, 1992, abandoned, which is a continuation of Ser. No. 555,397, Oct. 19, 1990, abandoned.

[30] Foreign Application Priority Data

Feb. 19, 1988 [AU] Australia .......................... PI6850/88

[51] Int. Cl.⁶ ...................... A61K 31/575; C07J 31/00
[52] U.S. Cl. ...................................... 514/182; 552/542
[58] Field of Search .......................... 552/542; 514/182

[56] References Cited

U.S. PATENT DOCUMENTS 3,931,403  1/1976  Saltzman ........................... 514/182
5,026,883  6/1991  Kosuge et al. ..................... 552/542

FOREIGN PATENT DOCUMENTS

88/01274  2/1988  WIPO .

OTHER PUBLICATIONS

Bridgewater et al, J. Biochemistry 82, (1962), pp. 285–290.
Foye, *Principles of Medicinal Chemistry* (1981), pp. 32–35.

*Primary Examiner*—Philip I. Datlow
*Attorney, Agent, or Firm*—Cushman Darby & Cushman

[57] ABSTRACT

The present invention relates to 24R-scymnol, including its preparation in substantially pure form and to its use in the treatment of liver dysfunction.

4 Claims, 6 Drawing Sheets

FIGURE 1

| Atom | GI | X | Y | Z | β11 | β22 | β33 | β12 | β13 | β23 |
|---|---|---|---|---|---|---|---|---|---|---|
| C(1) | 1.0 | 1440(6) | 1440(6) | 9449(16) | 37(4) | 39(4) | 220(27) | 16(3) | 34(9) | -9(9) |
| C(2) | 1.0 | 1103(6) | 1493(7) | 9561(17) | 32(4) | 64(6) | 210(28) | 10(4) | 28(9) | 39(11) |
| C(3) | 1.0 | 588(6) | 1395(6) | 8113(19) | 30(4) | 37(4) | 322(33) | 8(3) | 26(10) | 19(11) |
| C(4) | 1.0 | 966(5) | 1438(6) | 6389(16) | 26(3) | 33(4) | 271(29) | 3(3) | 15(8) | 4(9) |
| C(5) | 1.0 | 1342(6) | 2157(6) | 6217(15) | 32(4) | 37(4) | 201(25) | 11(3) | 10(8) | 14(9) |
| C(6) | 1.0 | 1717(6) | 2231(5) | 4522(15) | 31(3) | 31(4) | 188(24) | 6(3) | 7(8) | 20(8) |
| C(7) | 1.0 | 2458(5) | 1835(5) | 4397(14) | 27(3) | 31(3) | 175(23) | 4(3) | -10(8) | 2(8) |
| C(8) | 1.0 | 2940(5) | 1994(5) | 5922(13) | 28(3) | 32(3) | 113(18) | 7(3) | 11(7) | 10(7) |
| C(9) | 1.0 | 2534(5) | 1844(5) | 7591(13) | 29(3) | 24(3) | 128(19) | 11(2) | 15(7) | 4(6) |
| C(10) | 1.0 | 1862(5) | 2321(5) | 7716(14) | 34(3) | 30(3) | 147(22) | 13(3) | 14(8) | -5(7) |
| C(11) | 1.0 | 3028(6) | 1920(5) | 9154(14) | 40(4) | 26(3) | 151(21) | 11(3) | -4(9) | -5(8) |
| C(12) | 1.0 | 3740(5) | 1450(5) | 9004(14) | 33(3) | 25(3) | 160(20) | 6(3) | -11(8) | -12(7) |
| C(13) | 1.0 | 4142(4) | 1699(4) | 7597(12) | 21(3) | 23(3) | 109(17) | 2(2) | -1(6) | 11(6) |
| C(14) | 1.0 | 3645(5) | 1579(4) | 5878(12) | 24(3) | 17(2) | 122(17) | 2(2) | 2(7) | -3(6) |
| C(15) | 1.0 | 4145(5) | 1685(5) | 4360(14) | 24(3) | 35(3) | 146(20) | -1(3) | 12(7) | 9(8) |
| C(16) | 1.0 | 4870(5) | 1389(6) | 4957(13) | 27(3) | 34(3) | 145(19) | 1(2) | 8(7) | 2(7) |
| C(17) | 1.0 | 4790(4) | 1226(4) | 6894(13) | 21(3) | 22(3) | 143(17) | 1(2) | 7(6) | -0(6) |
| C(18) | 1.0 | 4406(6) | 2442(4) | 7532(16) | 41(4) | 14(2) | 229(26) | 2(3) | -13(10) | -21(7) |
| C(19) | 1.0 | 2054(7) | 3069(5) | 7654(20) | 51(5) | 20(3) | 333(35) | 13(3) | -05(13) | -14(10) |

FIGURE 1 (cont)

| | | | | | | | | |
|---|---|---|---|---|---|---|---|---|
| C(20) | 1.0 | 5494(5) | 1298(4) | 7854(13) | 26(3) | 19(2) | 159(21) | -2(2) | -8(7) | 2(6) |
| C(21) | 1.0 | 5399(6) | 1062(7) | 9713(15) | 33(4) | 47(4) | 174(24) | -2(4) | -20(8) | 14(9) |
| C(22) | 1.0 | 6083(5) | 858(5) | 7036(15) | 17(3) | 27(3) | 230(23) | 1(2) | -14(7) | -6(8) |
| C(23) | 1.0 | 6823(5) | 933(5) | 7900(15) | 21(3) | 29(3) | 222(25) | -2(2) | -11(8) | -14(8) |
| C(24) | 1.0 | 7430(6) | 621(7) | 6837(16) | 24(3) | 56(5) | 213(24) | -5(4) | 1(8) | 17(11) |
| C(25A) | 0.5 | 8156(10) | 1015(9) | 7589(30) | 29(6) | 21(5) | 163(47) | 8(4) | 20(15) | 6(14) |
| C(26A) | 0.5 | 8344(10) | 727(10) | 9311(27) | 32(6) | 25(6) | 145(41) | -2(5) | -18(15) | 5(14) |
| C(27A) | 0.5 | 8761(11) | 945(11) | 6237(28) | 25(6) | 37(7) | 181(43) | 3(6) | 7(14) | 14(15) |
| C(25B) | 0.5 | 8220(9) | 614(9) | 7522(28) | 24(5) | 21(5) | 158(44) | -4(5) | -1(15) | 6(14) |
| C(26B) | 0.5 | 8297(10) | 390(11) | 9364(28) | 23(5) | 38(7) | 162(44) | -6(5) | -15(15) | 13(16) |
| C(27B) | 0.5 | 8461(12) | 1387(10) | 7317(33) | 21(6) | 21(6) | 239(58) | -23(6) | -25(21) | 48(16) |
| O(3) | 1.0 | 254(4) | 737(5) | 8173(16) | 33(3) | 70(4) | 584(36) | -10(3) | 24(9) | 70(12) |
| O(7) | 1.0 | 2312(3) | 1123(4) | 4264(10) | 29(2) | 34(2) | 202(16) | -2(2) | 14(5) | -0(6) |
| O(12) | 1.0 | 3574(3) | 795(3) | 9087(9) | 32(2) | 28(2) | 167(13) | 8(2) | 14(5) | 17(5) |
| O(24) | 1.0 | 7325(4) | -105(4) | 6896(10) | 40(3) | 45(3) | 207(16) | 11(2) | 3(6) | -8(7) |
| O(26A) | 0.5 | 8960(9) | 1041(9) | 10010(21) | 43(6) | 47(6) | 193(34) | -7(5) | -6(13) | -14(13) |
| O(27A) | 0.5 | 8894(9) | 272(9) | 5979(24) | 43(6) | 43(6) | 291(41) | 14(5) | -21(15) | -5(15) |
| O(26B) | 0.5 | 9019(7) | 256(8) | 9733(21) | 29(5) | 47(6) | 217(34) | 0(5) | -11(11) | 15(13) |
| O(27B) | 0.5 | 8498(11) | 1496(9) | 5514(29) | 70(9) | 36(6) | 439(58) | -7(6) | 7(21) | 6(17) |
| C(Me) | 0.5 | 1347(10) | 4989(7) | 7141(18) | 120(10) | 34(4) | 272(34) | -29(6) | 34(18) | -2(12) |
| O(OH) | 0.5 | 1867(5) | 5417(5) | 7849(12) | 74(4) | 52(3) | 224(20) | -10(3) | 51(9) | 4(8) |
| H2O-A | 0.5 | 6083(12) | 4771(10) | 7153(26) | 79(10) | 54(8) | 271(47) | 6(7) | 4(20) | -29(17) |
| H2O-B | 0.5 | 9158(16) | 492(19) | 3260(29) | 122(17) | 178(23) | 244(44) | -39(17) | -1(24) | 12(30) |

R = 0.105
WR = 0.101

METHOD OF TREATING LIVER DYSFUNCTION WITH 24-R SCYMNOL

This application is a continuation-in-part of Ser. No. 07/863,318, filed Apr. 1, 1992, now abandoned which is a continuation of Ser. No. 07/555,397, filed Oct. 19, 1990, now abandoned. The entire contents of the applications having Ser. Nos. 07/863,318 and 07/555,397 are incorporated herein by reference.

BACKGROUND OF THE INVENTION

This invention relates to the compound 24R-scymnol, to the preparation of this compound in substantially pure form, and to the use thereof in the treatment of liver dysfunction.

In prior international Patent Application No. PCT/AU87/00281 now published as WO88/01274, there is disclosed a process for the isolation and preparation of an active principle by extraction from particular tissues of sharks. This active principle, now termed "isolutrol", was isolated in good yield from an aqueous extract of the livers and/or gall bladders of sharks, and the active component therein identified as 24R-(+)3α, 7α, 12α, 24,26-pentahydroxycoprostane-27-sodium sulphate ester (sodium 24R-scymnol sulphate).

SUMMARY OF THE INVENTION

It has now been found that 24R-scymnol can be prepared from the active component disclosed in the above prior International Patent Application, and that 24R-scymnol has activity in the treatment of liver dysfunction.

According to a first aspect of the present invention, there is provided the compound of the formula I, in substantially pure form:

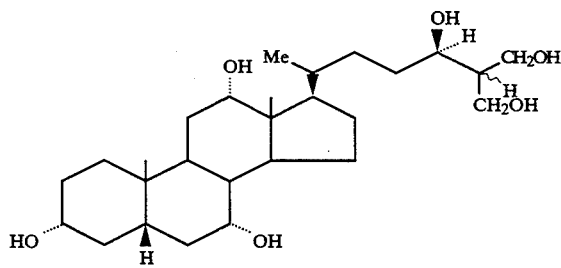

This compound, 24R-(+)-5β-cholestane-3α,7α,12α, 24,26,27-hexol, has been designated as 24R-scymnol.

For the purposes of this specification, the term "substantially pure" is intended to indicate that the composition is 24R-scymnol that is substantially free of any other enantiomer of scymnol.

The chemical structure of scymnol has been reported by Bridgewater et al. (1962) as 5β-cholestane-3α, 7α, 12α,24ε,26,27-hexol. However, the stereochemical configuration at the 24-position of scymnol was not identified, and there are three possibilities in the configuration at this position, namely 24R, 24S or a mixture of 24R and 24S. Bridgewater et.al. also reported that chemically synthesized scymnol was exactly identical with scymnol derived from natural shark's bile. This suggests that scymnol is the mixture of 24R and 24S compounds, since theoretically the synthesized scymnol should be produced in both 24R and 24S configurations on reduction with NaBH₄ of the ketone in the 24-position of the starting material as described by Bridgewater et.al.

The present invention also provides a method for the preparation of the compound of general formula I, which comprises the step of hydrolysis of a 24R-scymnol sulphate ester with an inorganic acid, preferably in the presence of barium chloride.

The process for the preparation of 24R-scymnol as broadly outlined above is particularly advantageous as it can be carried out using aqueous acids.

The present invention also provides a pharmaceutical composition for treatment of liver dysfunction, consisting essentially of substantially pure 24R-scymnol in an amount sufficient to treat liver dysfunction, together with a pharmaceutically acceptable carrier or diluent therefor.

This invention also provides a method of treating liver dysfunction comprising administering to a mammal in need of such treatment an amount of R-scymnol sufficient to effect said treatment.

BRIEF DESCRIPTION OF THE DRAWINGS

FIG. 1 is a tabulation (in two parts) of atomic parameters of 24R-scymnol;

DETAILED DESCRIPTION

Figure 2:
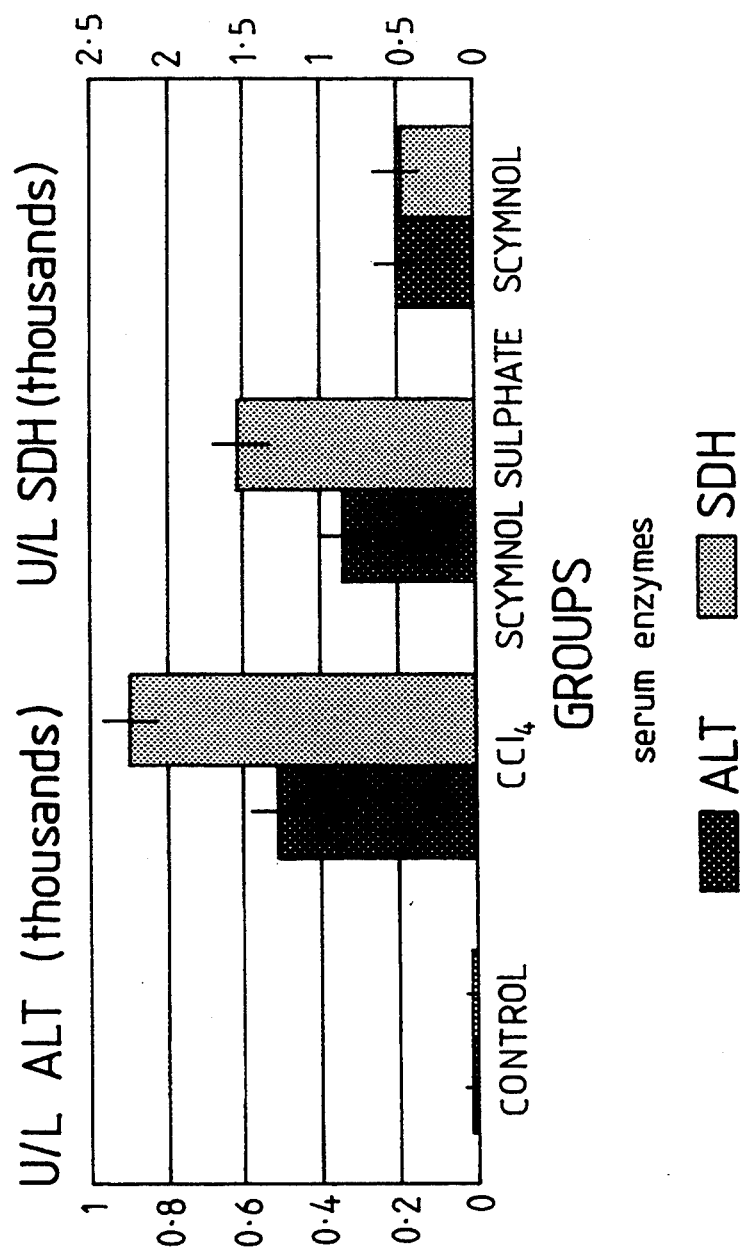
FIG. 2 shows hepatoprotection against carbon tetrachloride by R-scymnol and 24R-scymnol sulphate.

In accordance with a preferred procedure of the present invention, 24R-scymnol has been prepared by hydrolysis of sodium scymnol sulphate with dilute hydrochloric acid in the presence of barium chloride, to give a crystalline product. The physical and chemical data of the product are set out in Table 1:

TABLE 1

Physical and chemical data of 24R-scymnol.

| | |
|---|---|
| mp 183–184° C. (190° C.) (colorless plate), | H₂O insol, MeOH,EtOH sol AcOEt slightly sol, CHCl₃ insol |
| $(\alpha)_D{}^{25}$=40.40°(0.5c,in MeOH)(34%2°(0.9c,in ETOH)) | |
| High resolution mass; | calcd for C₂₇H₄₄O₄ (des-2H₂O) 432.6493 |
| | found 432.3247 |

IR ν KBr$_{cm^{-}}$:3400, 2950, 1480, 1380, 1080, 1040, 980, 920 max

¹H-NMR(in CD₃OD); δ(ppm): 3.95(1H,br), 3.80–3.50(6H,m), 3.48(1H,m), 2.40–2.15(2H,m), 2.10–1.10(23H,m), 1.07(3H,d, J=6.01Hz)0.91(3H,s), 0.71(3H,s)

¹³C-NMR(inCD₃OD); δ(ppm)74.8(d), 73.5(d), 73.0(d), 69.8(d), 62.7(t), 62.0(t), 50.0(t), 49.0(d), 48.1(s), 43.8(d), 43.6(d), 41.7(d), 41.1(t), 37.8(d), 37.2(t), 36.6(s), 36.5(t), 34.0(t), 33.0(t), 31.9(t), 30.3(t), 29.5(t), 28.5(d), 25.0(t), 24.0(q), 18.9(q), 13.8(q).

The stereochemical configuration at the 24-position of the compound was determined as R(+) by its crystallographical analysis and the specific optical rotation. The crystal data and atomic parameters of the compound are set out in Table 2 and FIG. 1, respectively.

In FIG. 1, fractional atomic coordinates (×10⁴) are given, with e.s.d.'s in parentheses, and anisotropic thermal parameters (Å²×10⁻⁴).

TABLE 2

Crystal data of 24R-scymnol $C_{27}H_{48}O_6 \cdot CH_3OH \cdot H_2O$, M=518.71, Orthorhombic, Space group
$P\ 2_12_12$, a=18.571(1), b=19.927(2), c=7.984(1)Å, V=2954.8Å$^3$,
Z=4, F(000)=1144, Dc=1.19 g/cm$^3$, Do=1.22 g/cm$^3$,
$\lambda$(Cu—K$\alpha$)=1.54180 Å, $\mu$(Cu—K$\alpha$)=7.9cm$^{-1}$, crystal size
0.2×0.2×0.4 mm.

The activity of 24R-scymnol in the treatment of liver dysfunction has been investigated. In prior International Patent Application No. PCT/AU87/00281, two assays have been designated to identify characteristic pharmacological activities of the substance, 24R-scymnol sulphate (or isolutrol). The bioassays, designated as (A) and (B), have been based on the following activities:

(A) the active principle prevented liver damage in mice caused by carbon tetrachloride; and (B) the active principle increased the respiration rate in mice when a toxic substance, such as nicotine, was administered.

These assays are useful in ascertaining the existence of activity, however it has been found that they are sometimes unreliable and not reproducible, indicating they are not reliable assays for measuring the degree of activity. 24R-scymnol has activity in these two bioassays, but it is difficult to make comparison of the degree of activity between isolutrol and 24R-scymnol. Accordingly, a new assay has been designed to reproducibly measure the degree of activity. This bioassay, designated as bioassay (C), measures tyrosine aminotransferase (TA) activity in liver of mice. TA is one of important enzymes in liver. The results of this assay are set out in Example 2 below.

In addition, to elucidate the possible mechanisms involved in mediating the hepatoprotective effects of 24R-scymnol and 24R-scymnol sulphate various biological features have been assayed. These assays included inhibition of the effects of hepatotoxicity in vivo, in which hepatotoxic responses of animals to carbon tetrachloride, acetaminophen (paracetamol) and α-amanitine were assessed, along with the acute effects of alcohol ingestion. The results of these assays are set out in Examples 4 to 7 below and demonstrate that 24R-scymnol has surprising, and unexpected, hepatoprotective effects, even when compared with 24R-scymnol sulphate.

The present invention also provides a pharmaceutical composition comprising 24R-scymnol, together with a pharmaceutically acceptable carrier or diluent therefor. By way of example, 24R-scymnol can be formulated as stable tablets after being mixed as a powder with a known carrier or bulking agent. Such pharmaceutical compositions may be used, for example, for the activation of liver function in the treatment of the diseases of the liver such as hepatitis, nephritis, diabetes, etc.

Further details of this invention will be apparent from the following Examples which illustrate the invention without limiting it in any way.

EXAMPLE 1

Preparation of 24R-scymnol

The active principle of shark's bile (500 mg) was dissolved in 7 ml of 1% HCl containing 400 mg of BaCl$_2$ and the mixture was heated for 5 h at 100° C. After cooling, the resulting solution was extracted three times with 50 ml of AcOH-BuOH (1:1). The organic layer was washed twice with H$_2$O. Removal of the solvent gave a yellow oil. The resultant residue was dissolved in MeOH and applied to reversed phase HPLC. 50 mg of 24R-scymnol was obtained.

EXAMPLE 2

BIOASSAY (C)—Measurement of TA Activity in Liver of Mice

Mice (5 weeks old) were orally administered 24R-scymnol sulphate, the active principle of shark's bile as disclosed in International Patent Application No. PCT/AU87/00281 (MD) (10 mg/kg), 24R-scymnol (10 mg/kg), or water (6:00 PM on the previous day, 9:00 AM on the day). After one hour from the last administration, the mice were forced to swim in a body of water at 35° C. After 4 hours swimming, the mice were sacrificed by decapitation and their livers were perfused with 0.145M KCl to remove blood. Half gram of liver was homogenized in 0.145M KCl and centrifuged at 10,000×g for 30 min. and TA activity in the supernatant was measured by the method of Diammondstone. The activity is shown as the amount of p-hydroxyphenyl pyruvic acid (p-HPP) produced by the enzyme reaction for 10 min.

The results of the comparison of the activities of the active principle and 24R-scymnol by the assay (C) are as follows:

| | TA activity (n-mole p-Hpp/mg protein/10 min. |
|---|---|
| Control | 1007 ± 49.6 |
| MD | 1322 ± 63.0** |
| 24R-scymnol | 1351 ± 29.2*** |

**: $P < 0.01$,
***: $p < 0.001$

The above results indicate that 24R-scymnol has almost the same activity as the active principle of the shark's bile.

EXAMPLE 3

GENERAL METHODS

The following materials and methods were used in Examples 4 to 7 hereinafter:

A. General Experimentation

Ultraviolet (U.V.) absorption spectra were determined on a Hitachi U3200 double beam spectrophotometer.

Fluorescence was determined on a Hitachi F-2000 fluorescence spectrophotometer.

B. Pharmacological Experimentation

Male Swiss mice were obtained from Monash University animal house and Australian Animal Resources aged at 8–10 weeks and weighed between 25–30 g. The animals were maintained in a temperature controlled animal house on a 12 hour light dark cycle and allowed food and water ad libitum.

Test animals received 5 mg/kg 24R-scymnol or 24R-scymnol sulphate intraperitoneally in 0.01 ml/g saline daily for seven consecutive days. Control animals were housed in the same conditions yet received no treatment. A vehicle control however was used in the first experimentation of carbon tetrachloride.

Hepatotoxins were administered i.p. on the eighth day, 24 hours after the last drug injection. Cardiac puncture was performed on mice anaesthetised with Nembutal 0.6 mg/kg in saline 24 hours after toxin administration and liver excised for use in histology and microsome preparation. Blood was centrifuged for 5 mins at 5,000 rpm and serum stored at −15° C. for further use.

C. Microsome Preparation

The liver was rapidly rinsed in ice-cold (4° C.) phosphate buffer 0.1M pH 7.4 to remove contaminating blood. Liver was homogenised in phosphate buffer (25% liver w/v) using a ultraturax homogeniser at setting 6 with 3 passes for 10 seconds. The homogenate was centrifuged at 4° C. (12,500 rpm) for 20 mins and the supernatant retained and centrifuged at 40,000 rpm for 60 mins in a Beckman Ultracentrifuge.

The microsomal plug was washed in the phosphate buffer and resuspended in 0.1M phosphate buffer pH 7.4 containing 20% glycerin (50% liver w/v) by agitation in a glass hand homogeniser. Suspended microsomes were frozen at −70° C. until required.

D. Histopathology

Hepatic tissues were taken from the largest lobe and fixed in 20 volumes of formalin/specimen volume for 3 days. After dehydration and clearing, liver was impregnated in molten paraffin and 7 μM sections cut. Sections were stained with Mayers acid haematoxylin and Putts eosin following a modified formula to that of Disbrey, B. D. et al. (1970). The modified steps were as follows:

| 1. | Mayers haematoxylin | 1 min |
|---|---|---|
| 2. | Rinse in tapwater | |
| 3. | Scotts tapwater substitute | 30 sec |
| 4. | Rinse in tapwater | |
| 5. | Putts eosin | 30 sec |
| 6. | Rinse in tapwater | |
| 7. | Dehydrate, clear in xylene, mount in D.P.X. | |

E. Estimation of Liver Function

Elevation of the serum enzymes alanine transaminase (ALT), sorbitol dehydrogenase (SDH) and lactate dehydrogenase (LDH) were used as an index of hepatotoxicity. Balazs et al. (1961) recognise that the serum enzymes mentioned increase with increasing hepatocyte necrosis and hence are useful and accurate indexes of hepatocellular injury in rats after hepatotoxin administration.

ALT was determined by the formation of a brown pyruvate hydrazone, quantitated colorimetrically according to the method of Rietman and Frankel (1957). SDH and LDH were determined from the absorbance change at 340 nm occurring after the addition of fructose and pyruvate respectively by the method of Gerlach, U. (1963) and Kachmar, J. F. (1976) respectively.

Additionally, serum triglycerides measured colorimetrically were also used as a measure of liver damage. The method was based on the selective extraction of triglycerides on the Hantzch reaction for formaldehyde according to Levy, A. L. (1972). Glucose levels in serum were also tested by the bioMerieux kit method to detect any hypoglycemia caused by hepatocyte damage.

F. Protein Estimation

These were performed by a modified version of the Lowry method (Markwell et al., 1978) with bovine serum as a standard.

G. Statistical Evaluation

All biological data were expressed here as mean ±S.E.M. and the statistical significance was evaluated as the t-test, difference between two means with a significance of $p \pm 0.05$.

EXAMPLE 4

Hepatoprotection Against Carbon Tetrachloride

The toxic effects of carbon tetrachloride on the liver have been investigated over many years with particular attention to the pathology, toxicology and biochemistry of $CCl_4$ induced by liver injury attributable to:

* $CCl_4$ being readily available in pure form,
* $CCl_4$ consistently produces liver injury in many species (the type and severity of injury to the liver can vary from triacylglycerol accumulation through necrosis to cirrhosis and cancer depending on dosage and method of application),
* $CCl_4$ is of considerable industrial and environmental importance and is a natural product.

A single dose of $CCl_4$ administered to a rat produces centrilobular necrosis and fatty degeneration of the liver. Electron microscopic examination of liver section from $CCl_4$ poisoned rats reveals early swelling, disorganization and degranulation of the endoplasmic reticulum but no equivalent damage to the mitochondria (thought to be due to the double membrane), particularly in the central zone. Depression of hepatic protein synthesis by $CCl_4$ has been confirmed which ultimately results in a reduction in the amount of serum triglycerides, since they leave the liver as lipoproteins.

In this study, the protective effects of 24R-scymnol and 24R-scymnol sulphate on several $CCl_4$ induced biochemical and morphological alterations were assessed.

A. MATERIALS AND METHODS (i) Pharmacological Experimentation

The Table below shows the protocol established for $CCl_4$ toxicity challenge.

| Days 1–7 | Day 8 | Day 9 |
|---|---|---|
| Bile salt injections | $CCl_4$ | sacrifice |

Eight groups of five male Swiss mice were divided into control and $CCl_4$ (0.01 mL/g 5% solution in olive oil) treated groups. A saline control group receiving 0.01 mL/g saline was challenged with $CCl_4$ after a week of injections. An untreated group received $CCl_4$ on day 8. All groups had unchallenged controls.

Cardiac puncture was performed on anaesthetised mice on day 9 (24 hours after $CCl_4$ injection), blood collected for serum assays and liver excised for use in histology and microsome preparation.

(ii) Determination of Hepatocellular Injury

Elevation of the serum enzymes ALT and SDH was used as an index of hepatotoxicity along with protein determination and histological assessment according to the methods in Example 3.

B. RESULTS

FIG. 2 shows that alanine transaminase activity was markedly increased 24 hours after the administration of $CCl_4$. (FIG. 2 shows the effect on serum enzymes after CCl₄ treatment. Mice were sacrificed 24 hours after CCl₄ administration (0.01 mL/g, 5% CCl₄) and treated prior according to the method. Each value in FIG. 2 represents the average ÷S.E.M. from 5 animals.) Pretreatment with 24R-scymnol significantly reduced this increase however 24R-scymnol sulphate did not. Sorbitol dehydrogenase levels in serum increased 100-fold above untreated mice 24 hours after CCl₄ administration. Both 24R-scymnol and 24R-scymnol sulphate afforded significant protection against the SDH leakage with 24R-scymnol being the greater of the two bile salts.

Liver histology determined 24 hours after CCl₄ administration showed that all mice sustained centrilobular liver cell necrosis. The magnitude of necrosis was reduced when pretreated with the bile salts, again with the greatest protection afforded by 24R-scymnol. Gross morphological analysis of mouse liver complemented the effects seen by microscopy.

Liver cell protein synthesising ability was markedly reduced upon CCl₄ administration 24 hours after administration. Mice pretreated with 24R-scymnol however lost no significant protein synthesising ability measured in the liver microsomes (Table 3).

No apparent harmful effects on the liver were observed after intraperitoneal injection of either bile salt. Liver histology and serum enzyme analysis confirmed healthy livers with no difference to controls. Before killing, it was noticed that those animals injected with the bile salts were groomed better than the other groups with shinier, healthier coats and displaying a much less aggressive and agitated behaviour.

TABLE 3

Effect on mice of carbon tetrachloride

| Treatment | Appearance | Protein (mg/mL) |
|---|---|---|
| Control | — | 12.7 ± 0.8 |
| CCl₄ | +++ | 9.3 ± 0.62 |
| 24R-Scymnol sulphate | ++ | 11.3 ± 0.4 |
| 24R-Scymnol | + | 11.7 ± 0.7 |

Mice were treated with bile salts as per Methods section for 7 days. All groups excluding the untreated were administered with 0.01 mL/g of a 5% solution CCl₄ on day 8 and all mice sacrificed on day 9. Protein content was estimated on microsomal samples according to the Methods section. Each value represents the average ± S.E.M. from 5 animals. ²Significantly different from the control value $p < 0.05$.
Hepatic tissue was graded for necrosis. Key: − no change; + slight change; ++ moderate change; +++ significant change.

Mice were treated with bile salts as per Methods section for 7 days. All groups excluding the untreated were administered with 0.01 mL/g of a 5% solution CCl₄ on day 8 and all mice sacrificed on day 9. Protein content was estimated on microsomal samples according to the Methods section. Each value represents the average ±S.E.M. from 5 animals. ² Significantly different from the control value $p < 0.05$.
Hepatic tissue was graded for necrosis. Key: −no change; +slight change; ++moderate change; +++significant change.

EXAMPLE 5

Hepatoprotection Against Acetaminophen

Acetaminophen (paracetamol) is a derivative of para-aminophenol and was introduced into clinical medicine as an anti-pyretic agent in the late nineteenth century. When taken in therapeutic doses, paracetamol does not cause any appreciable side effects. However liver injury will develop in all patients who ingest sufficient acetaminophen, becoming evident biochemically within 24–48 hours of the time of ingestion (Black, M. 1980).

Studies have shown that acetaminophen-induced liver-cell necrosis is not only mediated by a metabolite of the drug, but that the microsomal mixed-function oxidase system is importantly involved in its formation. Liver injury falls upon the centrizonal hepatocytes, in which the greatest lobular concentration of the microsomal mixed-function oxidase system is located (Black, M. 1980).

Although the mixed-function oxidase system is centrally involved in generating the acetaminophen toxic metabolite, this pathway plays a minor role in the overall disposition of the drug when it is ingested in therapeutic doses. Thus 85–90% of acetaminophen is normally metabolised by glucoronide or sulphate conjugation (both are saturable processes) leaving a relatively small amount to be metabolised via other pathways including the mixed-function oxidase system.

Extensive studies performed by Jollow et al., (1973) found that acetaminophen metabolites covalently bound to the liver with increased binding also increasing the degree of liver necrosis. The peak level of binding preceded the development of recognisable necrosis by at least one or two hours with maximum binding to liver occurring two hours after acetaminophen administration.

By administering doses of acetaminophen in excess of therapeutic dosage and hence forcing the involvement of the mixed-function oxidase system, in this assay it is determined whether 24R-scymnol and 24R-scymnol sulphate are able to inhibit the consequences of this system.

A. METHODS (i) Pharmacological Experimentation

Three groups of five male Swiss mice were intraperitoneally administered with 350 mg/kg acetaminophen on day 8. Two of the groups received the drug after receiving the usual weekly bile salt inoculation. The third group received the drug after no prior treatment and a fourth group was a control receiving no drug or treatment.

In a second series of experiments, 5 male Swiss mice were intraperitoneally administered with acetaminophen (350 mg/kg) and one hour later received 24R-scymnol i.p. (35 μg/g in saline). Five additional mice received 24R-scymnol i.p. (35 μg/g in saline) four hours post acetaminophen administration and another five mice used as treatment controls.

All mice were killed 24 hours after acetaminophen administration and blood and liver taken as before.

(ii) Determination of Hepatocellular Injury

Elevation of the serum enzymes, ALT, SDH and LDH and triglyceride levels were used as indices of hepatotoxicity according to the methods mentioned in Example 3 along with histopathological assessment.

B. RESULTS

All serum enzymes tested increased significantly 24 hours after acetaminophen administration. 24R-Scymnol was capable of significantly reducing hepatic damage when administered prior as indicated by significant reductions in all serum enzyme levels except triglycerides. 24R-Scymnol sulphate however only reduced SDH and LDH levels significantly.

The alanine transaminase increase in serum levels 24 hours after acetaminophen administration was significantly reduced when 24R-scymnol was administered 1 hour after the drug. Protection was afforded also against SDH and LDH increase when 24R-scymnol was administered 1 hour post acetaminophen as to was serum triglyceride decrease. No protection at all was noticed against acetaminophen at this dosage when 24R-scymnol was administered 4 hours post acetaminophen administration.

Figure 3:
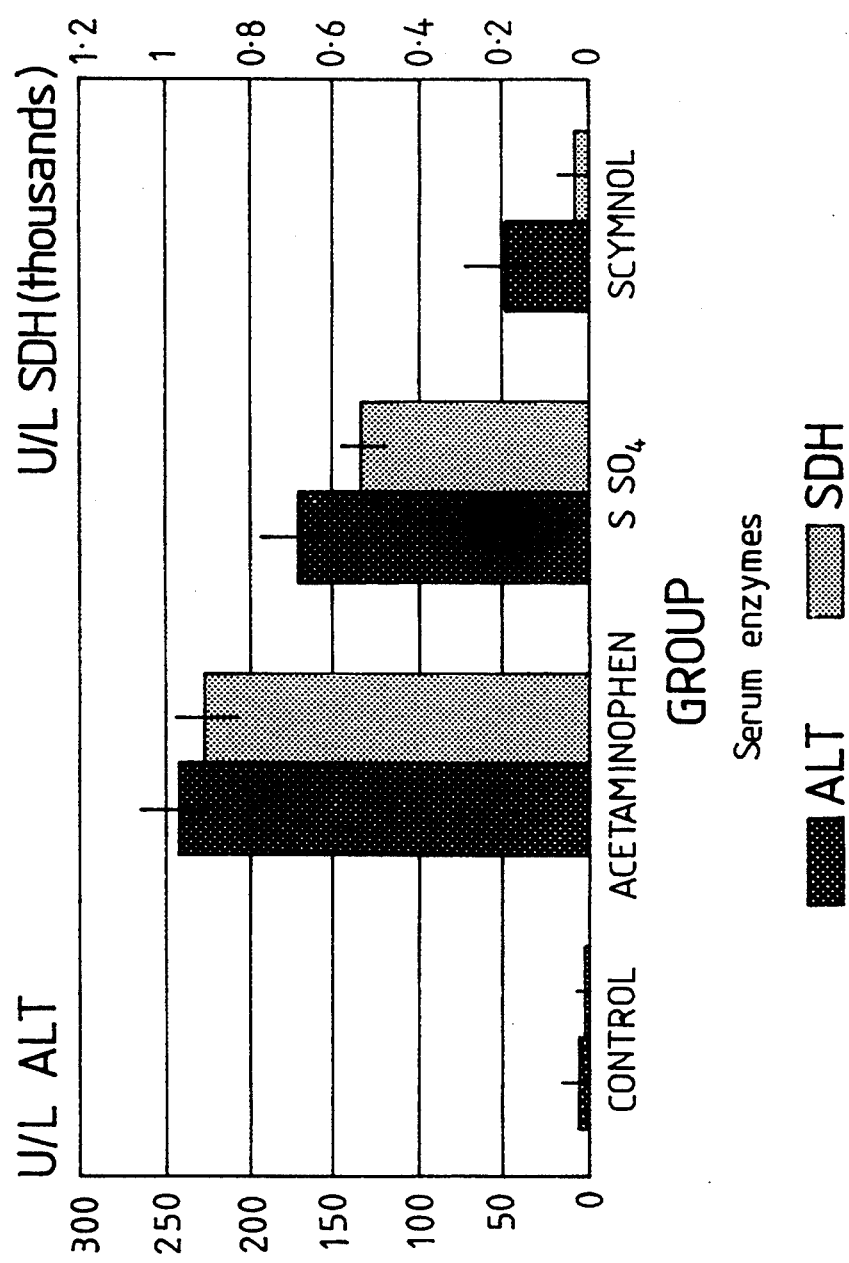
FIG. 3 shows hepatoprotection against acetaminophen by pretreatment with 24R-scymnol and 24R-scymnol sulphate.
Figure 4:
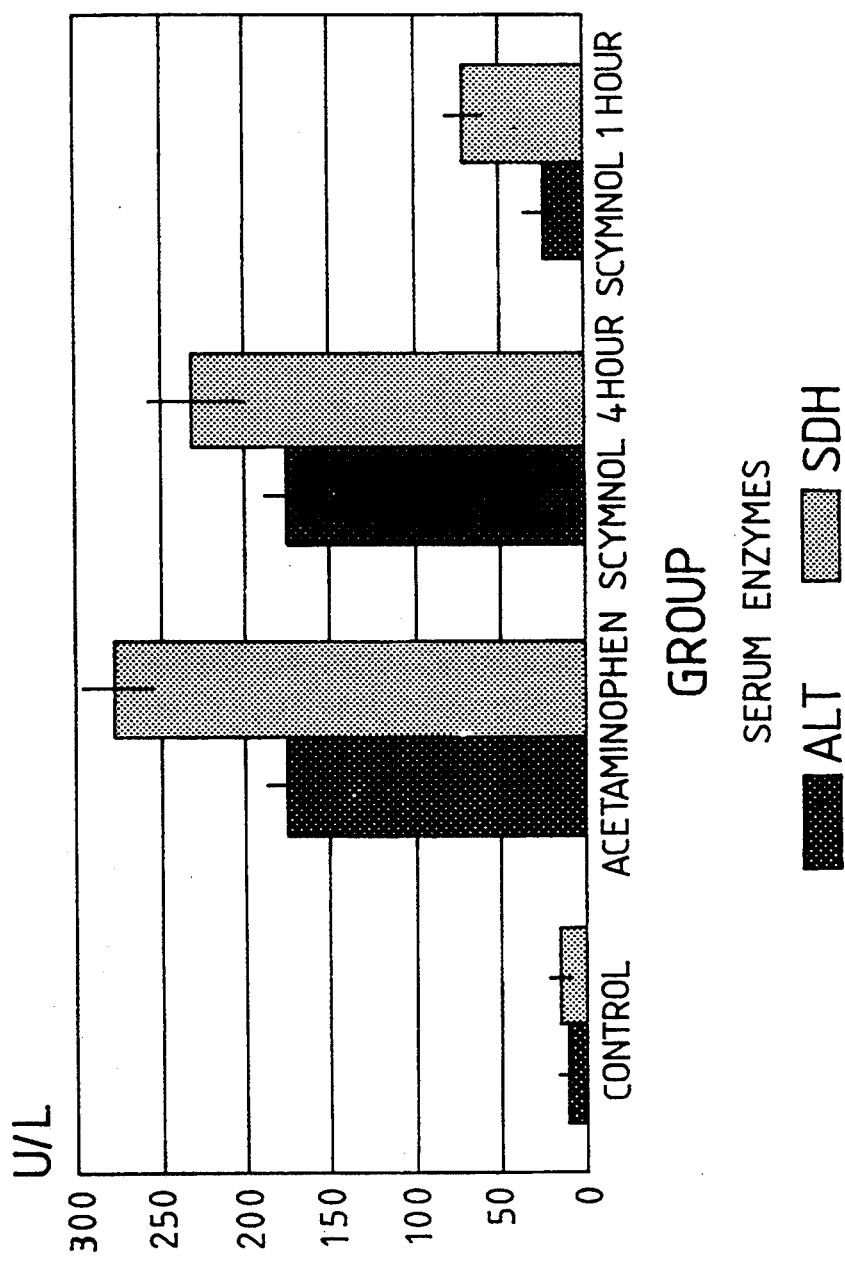
FIG. 4 shows hepatoprotection against acetaminophen by post-treatment with 24R-scymnol.

FIG. 3 shows serum enzymes ALT and SDH, 24 hours after acetaminophen administration. (FIG. 3 shows the effect on serum enzymes after acetaminophen administration. All animals received treatments according to the method and were sacrificed 24 hours after acetaminophen (350 mg/kg) administration. Each value represents the average ÷S.E.M. from 5 animals.) FIG. 4 shows the serum enzymes ALT and SDH after receiving 24R-scymnol post acetaminophen administration. (FIG. 4 shows the effect on serum enzyme levels of mice receiving acetaminophen prior to bile salt treatment. Mice were treated according to the methods and were sacrificed 24 hours after acetaminophen administration. Each value represents the average ÷S.E.M. from 5 animals.). Tables 4 and 5 summarise the effect of acetaminophen on serum triglycerides LDH and microsomal protein content.

Gross morphology of the liver suggested 24R-scymnol to be hepatoprotective against acetaminophen since necrosis was either non visible or very minute. The acetaminophen group showed levels of necrosis of slight to very damaged with 24R-scymnol sulphate very similar to this.

Histopathological assessment of liver sections showed centrilobular necrosis in all mice receiving acetaminophen. The magnitude of necrosis was significantly reduced by prior treatment with the bile salts, with 24R-scymnol livers containing only odd necrotic hepatocytes.

Generally the overall appearance of the mice showed a definite improvement in coat color and behaviour in the 24R-scymnol and 24R-scymnol sulphate treated mice as opposed to the controls. The acetaminophen mice showed evidence of fighting among the group, they were agitated and generally in poor physical condition.

TABLE 4

Effect of acetaminophen on mice after prior treatment with 24R-scymnol and 24R-scymnol sulphate.

| Treatment | LDH (U/L) | Triglycerides (mg/dL) | Protein (mg/mL) |
|---|---|---|---|
| Control | 32 ± 9 | 138 ± 8 | 12.7 ± 0.8 |
| Acetaminophen | 1997 ± 78[2] | 97 ± 6[3] | 10.9 ± 0.6[2] |
| 24R-Scymnol sulphate | 1101 ± 83[b] | 56 ± 2[3] | 10.5 ± 0.4[2] |
| 24R-Scymnol | 602 ± 29[b] | 117 ± 2[3] | 12.2 ± 0.3 |

Mice were treated as per the Methods section and administered with 350 mg/kg acetaminophen and sacrificed 24 hours later. Protein estimation was performed on liver microsomes. Each value represents the average ± S.E.M. [2]Significantly different from control p <0.05. [b]Although significantly different from control also different from acetaminophen treatment alone p <0.05.

TABLE 5

Effect on mice receiving 24R-scymnol post acetaminophen administration.

| Treatment | LDH (U/L) | Triglycerides (mg/dL) |
|---|---|---|
| Control | 32 ± 9 | 138 ± 8 |
| Acetaminophen | 1023 ± 98[2] | 74 ± 4[2] |
| 24R-Scymnol 1 hr | 550 ± 61[b] | 90 ± 5[b] |
| 24R-Scymnol 4 hr | 984 ± 111[2] | 70 ± 4[2] |

All mice except the control group received acetaminophen (350 mg/kg) and sacrificed 24 hours after. One group received 35 mg/kg scymnol 1 hour after acetaminophen, another received the bile salt 4 hours after acetaminophen administration. Each value represents the average ± S.E.M. from 5 animals. [2]Significantly different from control p <0.05. [b]Through significantly different from control also significantly different from acetaminophen alone.

EXAMPLE 6

Hepatoprotection Against Amanitine

α-Amanitine, a liver toxin (or amatoxin) produced by the fungus *Amanita phalloides* (the "green death cap") invariably causes death at a dosage of 0.2 μg/g mouse, though it holds true that different strains of the same species vary in sensitivity to the poison (Wieland, T. 1966).

An incubation or latency period occurs after exposure to the toxin, lasting up to 15 hours. A cholera-like period soon follows although there is no sign at this stage of liver toxicity. Conversely though at 48 hours after ingestion severe liver failure occurs with increased bilirubin and transaminase elevations and hypoglycemia. In severe cases the clinical deterioration may continue, with symptoms such as hepatic encephalopathy, coma and death (Piqueras, J. 1989).

Researchers have found that α-amanitine causes a poverty of protein metabolism due to the impairment of RNA synthesis. The liberation of glucose into the bloodstream is arrested due to damaged hepatocytes, unable to utilise glycogen in the normal manner, whilst lipid accumulation in the liver is due to the arrest of lipoprotein secretion (Choppin, J. 1979).

24R-scymnol and 24R-scymnol sulphate showed hepatoprotective effects with the toxins carbon tetrachloride and acetaminophen (see Examples 4 and 5 above) and as an extension of its ability to confer protection to the liver, experiments were modified to test the possible role in protection with the amatoxins.

A. METHODS (i) Pharmacological Experimentation

After the usual week of bile salt injections, five mice per group were intraperitoneally administered with 0.5 mg/kg α-amanitine in saline. A further five mice received the toxin after no prior treatment.

Blood and liver were taken in the usual manner, however 48 hours after toxin administration.

(ii) Determination of Hepatocellular Injury

Elevation of the serum enzymes ALT, SDH and LDH, along the serum glucose levels were used as indices of hepatocellular damage, along with histopathological assessment according to the methods in Example 3.

B. RESULTS

At the day of sacrifice one of the control mice had died. Since there appeared to be no evidence of fighting with the other mice in the group it was concluded that death was due to α-amanitine.

The gross morphological appearance of the remaining control mice liver approximated that of moderate necrosis apart from one which showed very slight necrosis. Those mice receiving 24R-scymnol showed no signs of liver cell necrosis whilst those receiving 24R-scymnol sulphate showed varying morphological characteristics ranging from none to moderate necrosis.

Histopathological assessment of liver sections showed hepatic necrosis in mice receiving α-amanitine along with loss of nucleus integrity, evident due to lack of nuclear staining. Prior bile salt treatment significantly reduced this necrosis and maintained the integrity of the hepatocyte nucleus.

Figure 5:
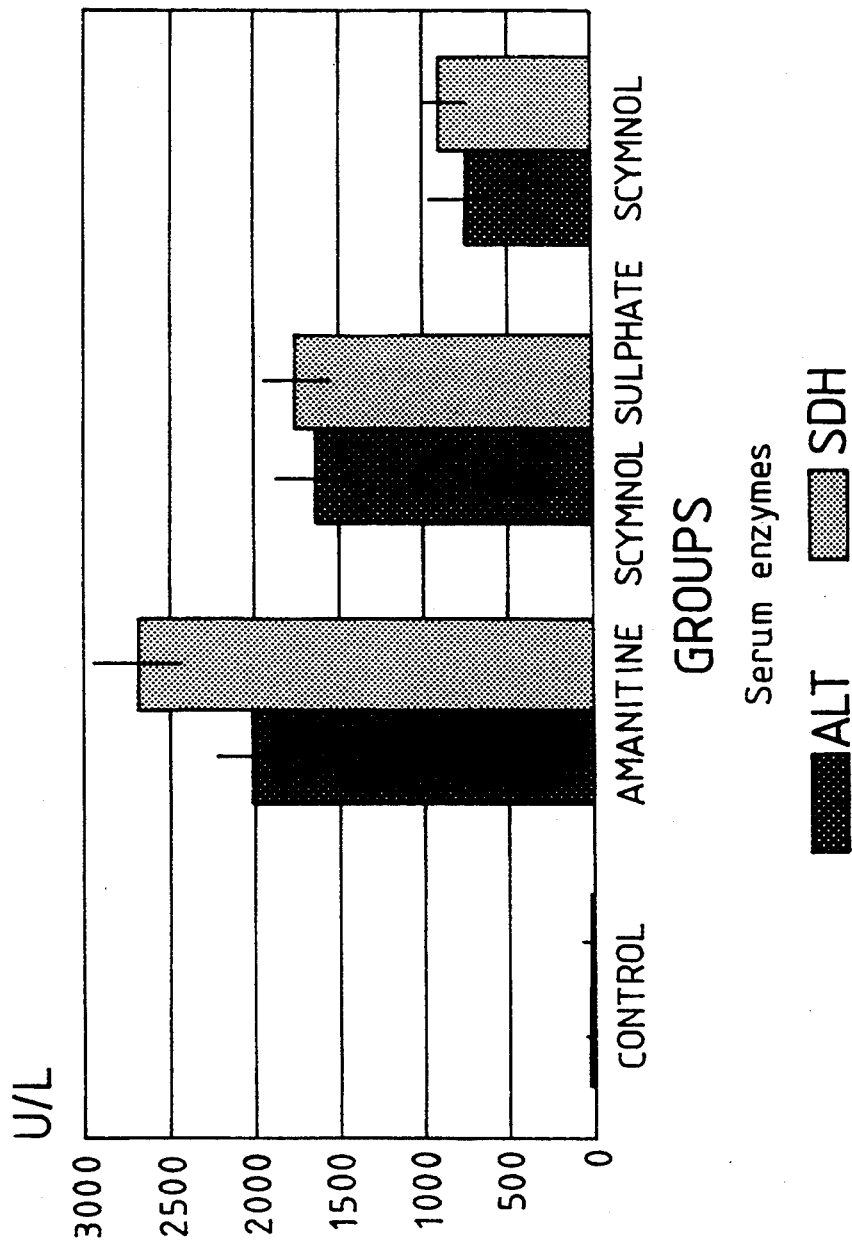
FIG. 5 shows hepatoprotection against α-amanitine by 24R-scymnol and 24R-scymnol sulphate.

FIG. 5 shows the serum enzymes ALT and SDH, 48 hours after α-amanitine administration. (FIG. 5 shows the effect on mice serum enzyme levels after α-amanitine treatment. Mice were treated according to the method and were sacrificed 45 hours after α-amanitine administration. Each value represents the average ÷S.E.M. from 5 animals.). Table 6 outlines the effects α-amanitine has on LDH, serum glucose levels and microsomal protein content.

All three liver enzymes; ALT, SDH and LDH were markedly increased 48 hours after α amanitine administration. Pretreatment with 24R-scymnol sulphate prior to administration of the poison did not significantly modify the increase in serum enzymes levels. Pretreatment with 24R-scymnol only afforded protection against ALT increase.

The hypoglycemia observed 48 hours after α-amanitine administration was significantly reduced with prior treatment with 24R-scymnol yet not 24R-scymnol sulphate.

Protein synthesis depletion observed in liver microsomes after α-amanitine treatment was significantly reduced upon pretreatment with both 24R-scymnol and 24R-scymnol sulphate.

TABLE 6

Effect on mice of amanitine.

| Treatment | LDH (U/L) | Glucose (mg/dL) | Protein (mg/mL) |
|---|---|---|---|
| Control | 21 ± 6 | 183 ± 4 | 13.2 ± 0.7 |
| Amanitine | 3741 ± 245[2] | 138 ± 2[2] | 7.6 ± 0.5[2] |
| 24R-Scymnol sulphate | 4193 ± 198[2] | 125 ± 1[2] | 11.3 ± 0.8[b] |
| 24R-Scymnol | 1810 ± 57[2] | 167 ± 2[b] | 10.7 ± 0.3[b] |

Mice were treated according to the method and sacrificed 48 hours after α-amanitine administration. Protein estimation was performed on liver microsomes according to the standard method. Each value represents the average ± S.E.M. from 5 animals. [2]Significantly different from control p <0.05. [b]Though significantly different from control also significantly different from α-amanitine treatment alone p <0.05.

EXAMPLE 7

Effects on Acute Ethanol Ingestion

Ninety to 98% of the alcohol that enters the body is completely oxidised to carbon dioxide and water (Hawkins et al., 1966). Ethanol is converted to acetaldehyde by at least 3 enzyme systems all of which are found extramitochondrially. These are alcohol dehydrogenase (ADH), catalase (CAT), and the microsomal ethanol oxidising system (MEOS), which uses NADPH in conjunction with molecular oxygen (Valenzuela, A. 1989).

Following acute ethanol ingestion, reduced glutathione (GSH) levels in the liver decrease whilst those of oxidised glutathione (GSSG) increase. This is in conjunction with an enhancement of hepatic lipoperoxidation which only occurs in conditions of maximal GSH reduction.

Tests were carried out to ascertain whether 24R-scymnol and 24R-scymnol sulphate are capable of reducing the effects of acute ethanol intoxication. In addition, the glutathione status of the liver was assessed, along with the serum enzymes alanine transaminase and sorbitol dehydrogenase since it has been demonstrated that they elevate after acute ethanol administration.

A. METHODS

(i) Pharmacological Experimentation

Male swiss mice received 2 g/kg ethanol administered as a 40% solution on day 8 after usual bile salt treatment. Animals were sacrificed 3 hours after ethanol intoxication and blood taken for routine serum assays and liver taken as before.

(ii) Determination of Hepatic Non-protein Sulphydryls

The protein was precipitated from aliquots of freshly homogenised liver with 25% $HPO_3$. Following the removal of precipitate by centrifugation at 100,000 g for 30 min the supernatant was assayed for GSH and GSSG according to the method of Hissin, P and Hilf, R. (1976). Standard curves were constructed each time samples were assayed, whilst supernatant was used the day of preparation.

(iii) Determination of Hepatic Lipid Peroxidation

Malondialdehyde is one of the products formed during microsomal lipid peroxidation which is capable of reacting with thiobartituric acid to give a species absorbing at 532 nm. Liver homogenate was assayed according to the method of Greenwald, R. G. (1985).

(iv) Determination of Blood Ethanol

Protein was precipitated from fresh blood samples by a mixture of 0.45% $ZnSO_4$ and 0.1N NaOH which gave a final pH of 7.0. The mixture was centrifuged at 4° C. and the supernatant used for ethanol measurements according to Hawkins et al. (1966).

(v) Determination of Hepatocellular Injury

Elevations of the serum enzymes, ALT and SDH were used as indices of hepatotoxicity according to the Methods in Example 3.

B. RESULTS

Table 7 illustrates the effect bile salts have on the serum ethanol levels 3 hours after ethanol intoxication. Table 8 illustrates the in vivo effect of acute ethanol treatment on mice with and without bile salts.

No increase in serum enzyme levels representative of hepatocellular injury were observed in the mice after 3 hours of ethanol intoxication.

TABLE 7

| Ethanol levels in mice after acute ethanol intoxication. | |
|---|---|
| Treatment | Ethanol mmol/mL |
| Control | 0.003 ± 0.001 |
| Ethanol | 0.156 ± 0.012[2] |
| 24R-Scymnol sulphate | 0.097 ± 0.007[b] |
| 24R-Scymnol | 0.103 ± 0.009[b] |

Mice were treated according to the methods section and sacrificed 3 hours after ethanol administration. Each value represents the average ± S.E.M. from 5 animals. [2]Significantly different from untreated value p <0.05.

TABLE 7-continued

Ethanol levels in mice after acute ethanol intoxication.

| Treatment | Ethanol mmol/mL |
|---|---|

[b]Significantly different from both untreated and control values p < 0.05.

TABLE 8

Effects of acute ethanol on mice.

| Treatment | mg/100 g GSH | mg/100 g GSSG | MDA nmol/mg protein/30 min |
|---|---|---|---|
| Control | 683 ± 32 | 156 ± 10 | 0.43 ± 0.008 |
| Ethanol | 504 ± 30[2] | 196 ± 12[2] | 0.52 ± 0.011[2] |
| 24R-Scymnol SO$_4$ | 600 ± 41[b] | 183 ± 15[2] | 0.49 ± 0.010[b] |
| 24R-Scymnol | 613 ± 27[b] | 187 ± 11[2] | 0.50 ± 0.009[b] |

Mice were treated according to the Method section and sacrificed 3 hours after ethanol administration. Each value represents the average ± S.E.M. from 5 animals. [2]Significantly different from control group p <0.05. [b]Though significantly different from this data is also significantly different from ethanol treatment alone p <0.05.

REFERENCES

Balazs, T., Murray, T., McLaughlan, J. and Grice, H. (1961). Hepatic tests in toxicity studies on rats. Tox. App. Pharm. 3, 71–79.

Black, M. (1980). Acetaminophen hepatotoxicity. Gasteroenterol 78,382–392.

Bridgewater, R. J., Briggs, T. and Haslewood, G. A. D. (1962). Comparative studies of bile salts. XIV. Isolation from shark bile and partial synthesis of scymnol. Biochem. J. 82, 285–290.

Choppin, J. and Deplaces, A. (1979). The action of silybin on the mouse liver in α-amanitine poisoning. Drug Res. 29, 63–68.

Disbrey, B. D. and Rack, J. H. (1970). Histological Laboratory Methods (Ed. Livingstone, E.). Longman Group LTD. pp.100–102.

Gerlach, U. (1963). Oxidoreductases, Transferases. In Methods of enzymatic analysis. (Ed. Bergmeyer, U. H.). Chemie, Verlag. Weinheim, Basel. Volume 3, pp.112–114.

Greenwald, R. G. (1985). Lipid peroxidation measurement. CRC Handbook of Methods for Oxygen Radical Research. CRC Press, Florida U.S.A. pp.204–205.

Hawkins, R. D., Kalant, H. and Khanna, J. M. (1966). Effects of chronic intake of ethanol on rate of ethanol metabolism. Can. J. Phys. Pharm. 44, 241–257.

Jollow, D., Mitchell, J., Potter, W., Davis, D., Gillette, J. and Brodie, B. (1973). Acetaminophen-induced hepatic necrosis: role of covalent binding in vivo. J. Pharm. Exp. Ther. 187, 195–202.

Kachmar, J. F. and Moss, D. W. (1976). Enzymes. Fundamentals of Clinical Chemistry. (Ed. Tietz, N. W.). W. B. Saunders Company, Toronto, Canada. Chapter 12, pp.657–659.

Levy, A. L. (1972). Determination of triglycerides by the hantzsch condensation reaction. Ann. Clin. Lab. Sci. 2, 474–479.

Markwell, M. A. K., Haas, S. M., Bieber, H. L. L. and Talbert, N. E. (1978). A modification of the Lowry procedure to simplify protein determination in membrane and lipoprotein samples. Analytical Chemistry. 87, 206–210.

Piqueras, J. (1989). Hepatotoxic mushroom poisoning: diagnosis and management. Mycopathol. 105, 99–110.

Reitman, S. and Frankel, S. (1957). A colorimetric method for the determination of serum glutamic oxaloacetic and glutamic-pyruvic transaminases. Amer. J. Clin. Path. 28, 56–63.

Valenzuela, A., Bustamante, J., Videla, C. and Guerra, R. (1989). Effects of silybin dihemisuccinate on the ethanol metabolizing systems of the rat liver. Cell. Biochem. Func. 7, 173–178.

Wieland, T. (1966). Poisonous principles of mushrooms of the genus Amanita. Sci. 159, 946–952.

We claim:

1. A method of treating liver dysfunction comprising administering to a mammal in need of such treatment an amount of 24R-scymnol sufficient to effect said treatment.

2. A method according to claim 1 wherein said treatment comprises in vivo inhibition of hepatotoxic effects.

3. A method according to claim 2, wherein said treatment comprises in vivo inhibition of the acute effects of ethanol ingestion.

4. A method according to claim 2, wherein said treatment comprises in vivo inhibition of acetaminophen-induced liver damage.

* * * * *

UNITED STATES PATENT AND TRADEMARK OFFICE
CERTIFICATE OF CORRECTION

PATENT NO. : 5,451,575
DATED : September 19, 1995
INVENTOR(S) : Kosuge, et. al.

It is certified that error appears in the above-indentified patent and that said Letters Patent is hereby corrected as shown below:

Title page, item [30] under Foreign Application Priority Data, insert--
PCT    PCT/AU89/00064    02/16/89--.

Signed and Sealed this

Second Day of July, 1996

Attest:

BRUCE LEHMAN

Attesting Officer    Commissioner of Patents and Trademarks